United States Patent [19]

Gray et al.

[11] Patent Number: 4,579,114
[45] Date of Patent: Apr. 1, 1986

[54] MOUTH TO MOUTH RESUSCITATION DEVICE

[75] Inventors: Thomas C. Gray, Flagstaff; Michael A. Rovedo, Parks; Richard L. Cook, Flagstaff, all of Ariz.

[73] Assignee: Wisdom Corporation, Parks, Ariz.

[21] Appl. No.: 540,356

[22] Filed: Oct. 11, 1983

[51] Int. Cl.$^4$ ............................................. A61M 16/00
[52] U.S. Cl. ................................ 128/203.11; 137/512
[58] Field of Search ................. 128/202.28, 202.29, 128/203.11, 205.13, 204.26; 137/512.3, 512

[56] References Cited

U.S. PATENT DOCUMENTS 1,040,766 10/1912 Roth ..................................... 137/512
3,017,880 1/1962 Brook .............................. 128/203.11

FOREIGN PATENT DOCUMENTS 1248475 8/1967 Fed. Rep. of Germany ......................... 128/204.26
1204930 1/1960 France ............................. 128/203.11

Primary Examiner—Henry J. Recla
Attorney, Agent, or Firm—Owen, Wickersham & Erickson

[57] ABSTRACT

A disposable mouth to mouth resuscitation device includes a one way valve for preventing the victim's breath, saliva, mucus or disease agents from contact with the resuscitator's mouth or respiratory tract. The one way valve is in a plastic body from which extends a curved airway tube for placing in the victim's mouth. At the other end of the plastic body is a flexible tube leading to a mouth piece at its opposing end, for insertion into the mouth of the resuscitator. A mouth and nose mask is connected to the plastic body, adjacent to the curved airway tube, for sealing over the nose and mouth of the victim during resuscitation. When the victim exhales, his breath and other exhaled materials are exhausted through a side port in the plastic body and into the atmosphere. The flexible tube, the mouth and nose seal and the location of the exhaust port allow the resuscitator to have one hand free to perform, when necessary, cardio-pulmonary resuscitation, monitoring of vital signs, or steps for stemming the flow of blood.

2 Claims, 6 Drawing Figures

MOUTH TO MOUTH RESUSCITATION DEVICE

BACKGROUND OF THE INVENTION

The invention relates to mouth to mouth resuscitation equipment, and more specifically to a disposable resuscitation device which protects the resuscitator from contamination while permitting him freedom of movement and use of at least one hand for other life saving functions.

Conventional mouth to mouth resuscitation equipment exhibits several problems. The equipment is relatively expensive to manufacture, and therefore must be rendered reuseable by sterilization. Also, the devices fail to protect the resuscitator from breath, foreign matter and contaminated liquids exhaled by the victim. Another disadvantage is that the conventional resuscitator devices have not permitted the resuscitator sufficient movement to perform other life saving functions while operating the device.

Harris U.S. Pat. No. 3,957,046 disclosed a mouth to mouth resuscitation device of simple design and construction, inexpensive in cost so as to be disposable after use. However, the Harris Patent did not solve the other problems associated with conventional resuscitation devices, as does the present invention described below.

SUMMARY OF THE INVENTION

The present invention overcomes the deficiencies of prior devices by providing a means by which the victim's mouth and nose can be sealed off during resuscitation and a means by which exhalation can occur automatically, so that at least one of the resuscitator's hands can be freed. The invention also provides a means enabling the resuscitator to change his position while administering resuscitation, and allows the resuscitator to avoid contamination through contact with exhaled fluids and foreign matter of the victim.

These advantages are accomplished by a disposable mouth to mouth resuscitation structure comprising a flexible air tube for reaching from the victim to the resuscitator, with a mouth piece for the resuscitator connected to one end of the flexible air tube, and a valve body connected at its other end to the opposite end of the air tube. The valve body has a lower end from which extends a victim airway tube. The valve body includes a one-way valve means for passing air from the flexible air tube through the valve body and through the airway tube to the victim, but for preventing back flow of fluids from the victim through the valve body, and it includes venting means for venting to atmosphere, fluids entering the valve body from the victim. Preferably, there is included a mouth and nose mask connected to the lower end of the valve body, for sealing off the victim's mouth and nose, by downward pressure on the mask during resuscitation. The victim airway tube of the device may be curved, terminating in an end oriented toward the victim's palate, serving as a tongue depressor and assuring that the open end will not be blocked.

It is therefore among the objects of the invention to prevent contamination of, free the hands of and allow movement of the resuscitator, through the provision of a disposable, compact, inexpensively produced mouth to mouth resuscitation device having a flexible tube of sufficient length to enable the resuscitator to move around while administering resuscitation, with a one-way valve assembly at the victim's end of the flexible tube, for admitting air delivered to the victim but preventing back flow of the victim's exhaled fluids through the air tube to the resuscitator and venting such fluids to atmosphere. These and other objects, advantages, features and characteristics of the invention will be apparent from the following description of a preferred embodiment, considered along with the accompanying drawings.

DESCRIPTION OF A PREFFERED EMBODIMENT

Figure 1:
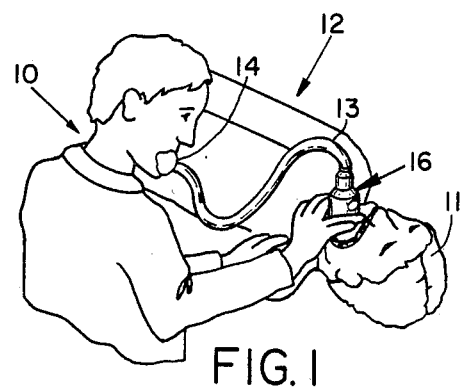
FIG. 1 is a perspective view showing a disposable mouth to mouth resuscitation device of the invention being used by a resuscitator to administer resuscitation to the victim.

In the drawing, FIG. 1 shows a resuscitator 10, or person administering mouth to mouth resuscitation, and a victim 11 to whom the resuscitation is being administered. The resuscitator is using a disposable mouth to mouth resuscitation device 12 according to the invention, including a flexible air tube 13, a resuscitator mouth piece 14 at the resuscitator's end and a valve body 16 at the victim's end.

Figure 2:
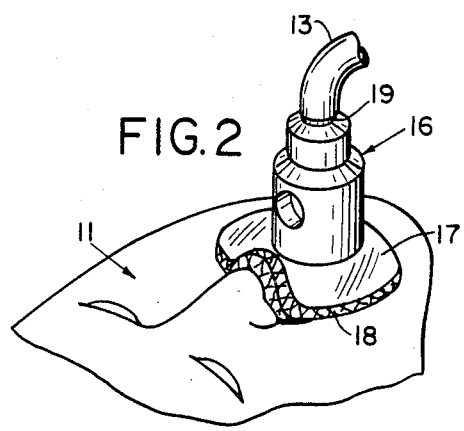
FIG. 2 is a perspective view showing a portion of the mouth to mouth resuscitation device including a mouth and nose mask positioned on the victim.

As shown in FIG. 2, the resuscitation device of the invention preferably includes a mask 17 for sealing over the mouth and nose of the victim 11. The mask 17 may be secured to the lower end of the valve body 16 by adhesive, for example, or other suitable bonding, and is preferably of a resilient material, particularly around its outer edge 18, which may be of a soft, pliable elastomeric material. As shown in FIG. 1, for establishing a seal over the victim's nose and mouth it may be necessary to apply a small amount of downward pressure on the mask 17 during resuscitation.

Figure 3:
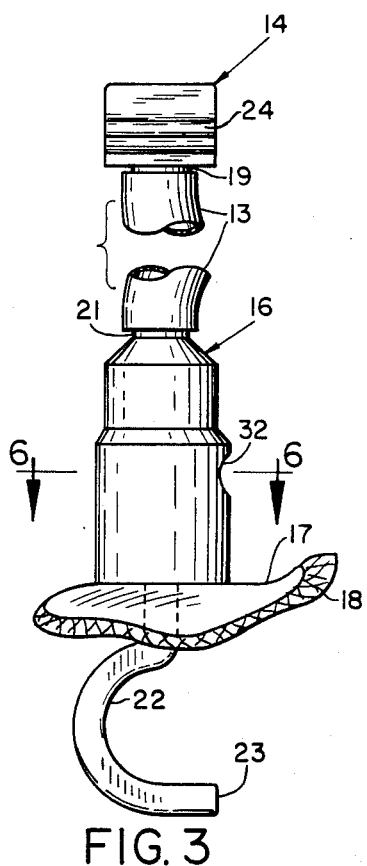
FIG. 3 is a side elevational view of the device, partially fragmented not showing the full length of the flexible air tube.
Figure 4:
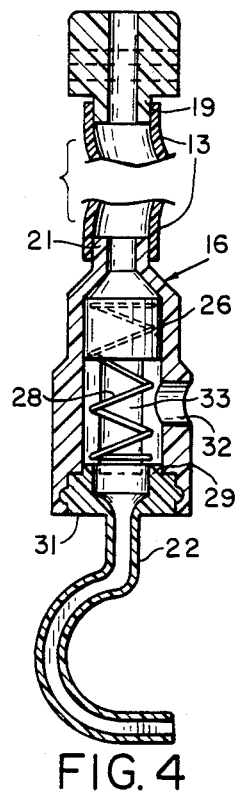
FIG. 4 is a sectional elevational view, looking in the same direction as FIG. 3, from a plane cutting through the center of the device, as indicated by the line 4—4 in FIG. 6. The mouth and nose mask are not shown in FIG. 4.
Figure 5:
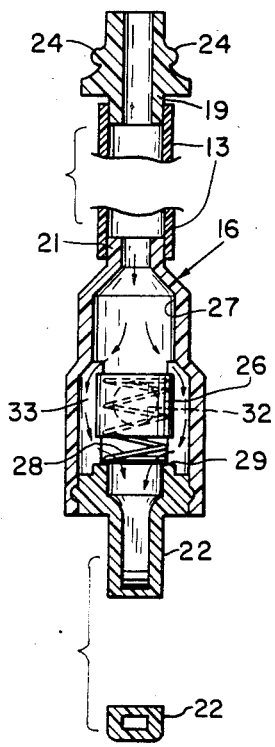
FIG. 5 is a sectional view of the device taken at right angles to the view shown in FIG. 4, as indicated by the line 5—5 in FIG. 6. The mouth and nose mask are not shown in FIG. 5.

FIG. 3 shows the resuscitation device 12 in side view, including the mouth and nose mask 17, and with the flexible air tube 13 fragmented and shortened (as also in FIGS. 4 and 5) for purposes of these drawings. The flexible air tube 13 is press-fit onto nipples 19 and 21 in the typical fashion on the resuscitator's mouth piece 14 and the top end of the valve body 16, respectively, as shown in all of FIGS. 2, 3, 4 and 5. As also shown in FIGS. 3 through 5, a victim airway tube 22 extends from the lower end of the valve body 16, and it may be of a curved or hooked configuration as shown. Its lower, open end 23 is so positioned as to be oriented toward the victim's palate when in use. The curved airway tube 22 thus serves as a form of tongue depressor assuring that the open end 23 does not become blocked during resuscitation.

As illustrated in FIGS. 3, 4 and 5, the resuscitator's mouth piece 14 may be shaped so as to include gripping ridges 24 for the resuscitator's teeth (see particularly FIG. 5).

As illustrated, the valve body 16 preferably is of a generally tapered shape, for purposes which will be apparent from FIGS. 4 and 5. The body 16 houses a slide valve assembly including a slideable valve spool or piston 26 which fits closely and slideably within an internal channel 27. Preferably, although not necessarily, the channel 27 and the valve piston 26 are cylindrical. The vave piston 26 is biased upwardly, toward its normal position shown in FIG. 4, by a light compression spring 28 which may fit up into the piston 26, which may be hollow and open from below. At its lower end, the spring 28 bears against a suitable seat, which may be provided by projections 29 integral with a base portion 31 of the victim airway tube 22, which may be snapped into place in connection with the valve body 16 after the valve piston 26 and spring 28 have been assembled inside. The base portion 31 is then bonded to the valve body, as by ultrasonic bonding.

It is therefore seen that the one-way valve assembly is closed in the normal position shown in FIG. 4. Air or other fluid cannot move in either direction in the flexible air tube 13, except under pressure from the resuscitator 10, whereby the valve piston 26 is forced downwardly against the compression spring 28. In the normal valve position of FIG. 4, any fluids exhaled by the victim enter the vave body through the victim airway tube 22, and are vented through an opening 32 to atmosphere.

FIG. 5 shows the position of the valve piston 26 when the resuscitator 10 is delivering air through the flexible air tube 13 to the victim 11. The piston 26 is in a lowered position, under a small to moderate amount of air pressure from the resuscitator 10, blocking off the venting piston is below the tops of side channels 33, as can be seen in FIG. 5. However, the side channels 33 are ineffective to pass fluid when the top of the valve piston 26 is above the tops of the side channels.

Figure 6:
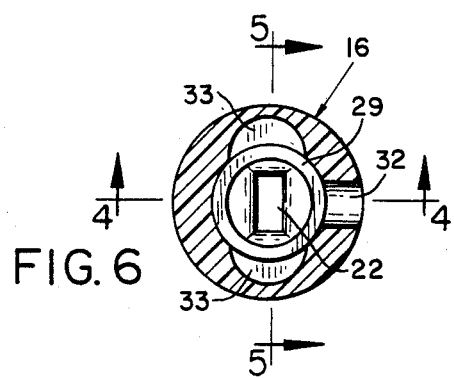
FIG. 6 is a sectional plan view, as viewed along the line 6—6 in FIG. 3, again not showing the mouth and nose mask.

FIG. 6 shows the valve body 16 and side channels 33 in sectional plan view. As seen therein, the channels 33 may comprise arcuate recesses molded into the inner wall of the thicker lower portion of the valve body 16.

In operation of the resuscitation device 12, the airway tube 22 is placed in the victim's mouth with the outside curved portion toward the victim'cheek, then rotated ninety degrees so that the outside curved portion depresses the tongue, keeping the victim's air passage open. The mouth and nose seal 17 is placed flush against the victim's mouth, and against the nostrils. The resuscitator 10 simultaneously places the mouthpiece in his mouth, gripping the mouthpiece in his teeth and breathing air into the lungs of the victim. Because the resuscitator is mobile and has the use of at least one hand he may, if needed, perform cardiopulmonary resuscitation, check vital signs or stem the flow of blood. Because of the flexible air tube 13, the resuscitator is able to avoid contamination by contact with the fluids and breath of the victim exiting the exhaust port 32.

To those skilled in the art of which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A mouth to mouth resuscitation device, comprising:
   (a) a flexible air tube for reaching from a victim to a resuscitator;
   (b) a mouth piece for the resuscitator, connected to one end of the flexible air tube;
   (c) a valve body having a passageway extending therethrough, said passageway connected at one end therefore to the air tube and being open at its opposite end, a base member mounted in said opposite open end and being formed with a victim airway hollow tube extending therefrom, the valve body including one-way valve means in said passageway for passing air from the air tube through the passageway and through the airway tube to the victim, and for preventing backflow of fluids from the victim through the passsageway and to the flexible air tube, said valve body including, with venting means for venting to atmosphere, fluids entering the passageway from the victim, wherein the victim airway tube is curved and of sufficient rigidity to depress the victim's tongue when its end is oriented toward the victim's palate, wherein the one-way valve means comprises a cylindrical bore in said passageway defining a valve seat at the one end thereof, a valve piston slidably mounted in said bore having one end engageable with said valve seat and spring means urging the valve piston toward said valve seat in a closed position, there being an exhaust port in a wall of the valve body normally communicating with the bore of the valve body and the airway tube, serving as said venting means, the port being axially spaced from the valve seat, but blocked by the piston when air is admitted under pressure from the air tube to force the valve piston away from the valve seat, and including recess means formed in a portion of the valve body wall along said bore between said valve seat and the opposite end of said bore and being angularly spaced from said port for establishing air communication from the one end of the valve body to the victim airway tube only when the valve piston is moved away from said seat to block said port, said spring means comprising a spring having one end supported on said base member and its other end bearing against the opposite end of the valve piston.

2. The resuscitation device of claim 1, further including a mouth and nose mask connected to the lower end of the valve body, for sealing off the victim's mouth and nose by downward pressure on the mask during resuscitation.

* * * * *

UNITED STATES PATENT AND TRADEMARK OFFICE
CERTIFICATE OF CORRECTION

PATENT NO. : 4,579,114
DATED : April 1, 1986
INVENTOR(S) : Thomas C. Gray, Michael A. Rovedo & Richard L. Cook It is certified that error appears in the above-identified patent and that said Letters Patent are hereby corrected as shown below:

```
Column 3, line 51, "victim'cheek" should read --victim's cheek--
Column 4, line 19, "therefore" should read --thereof--
```

Signed and Sealed this

Fifteenth Day of July 1986

[SEAL]

Attest:

Attesting Officer

DONALD J. QUIGG

Commissioner of Patents and Trademarks